United States Patent

Han et al.

Patent Number: 5,977,394
Date of Patent: Nov. 2, 1999

[54] SILYL THIOALKENE COMPOUND AND METHOD FOR THE PREPARATION THEREOF

[75] Inventors: Li-Biao Han; Masato Tanaka, both of Tsukuba, Japan

[73] Assignee: Japan as represented by Director General of Agency of Industrial Science and Technology, Japan

[21] Appl. No.: 09/261,387

[22] Filed: Mar. 3, 1999

[30] Foreign Application Priority Data

Mar. 13, 1998 [JP] Japan .................................. 10-062575

[51] Int. Cl.[6] ....................................................... C07F 7/08
[52] U.S. Cl. ................................................................ 556/427
[58] Field of Search ............................................. 556/427

[56] References Cited

U.S. PATENT DOCUMENTS 5,587,503 12/1996 Heider et al. ............................ 556/427
5,639,887 6/1997 Powell et al. ............................ 546/293

OTHER PUBLICATIONS

A. Carpita et al., *Tetrahedron Letters*, 30(20), 2699–2702 (May 1989).
*Chemical Abstracts*, 124:289151m (Jun. 1996).

*Primary Examiner*—Paul F. Shaver
*Attorney, Agent, or Firm*—Wenderoth, Lind & Ponack

[57] ABSTRACT

Disclosed is a silyl thioalkene compound, as a class of organosilicon compounds, represented by the general formula $$R(-CSAr=CHSiX_3)_n,$$

in which the subscript n is 1 or 2, R is, when n is 1, a hydrogen atom or unsubstituted or substituted monovalent hydrocarbon group or, when n is 2, a divalent hydrocarbon group, Ar is an unsubstituted or nucleus-substituted aromatic monovalent aromatic hydrocarbon group and X is a halogen atom, a monovalent hydrocarbon group or hydrocarbyloxy group, having usefulness as an intermediate in the synthesis of various precision organic chemicals. The compound, of which X is a halogen atom $X^1$, can be prepared, for example, by the reaction of an alkyne compound of the general formula $$R(-C\equiv CH)_n,$$

with a silyl sulfide compound of the general formula $$ArS-SiX^1_3,$$

in the presence of a platinum complex catalyst. The compound, of which X is a monovalent hydrocarbon group or a hydrocarbyloxy group, can be derived from the above obtained halogen-containing compound.

12 Claims, No Drawings

SILYL THIOALKENE COMPOUND AND METHOD FOR THE PREPARATION THEREOF

BACKGROUND OF THE INVENTION

The present invention relates to a novel silyl thioalkene compound having a silicon atom and a sulfur atom in the molecule, which is useful as an intermediate in the synthesis of various kinds of organic compounds, as well as to a method for the preparation of the compound.

A silyl thioalkene compound is a compound having a silicon atom and a sulfur atom in the molecule so that the compound is useful in the synthetic preparation of an organic compound having a sulfur atom by undertaking a position-specific or stereospecific coupling reaction between the compound and an organic halogen compound in the presence of a catalyst readily to form a carbon-carbon linkage and in the preparation of a diol or enol ether compound having a sulfur atom in the molecule by undertaking the so-called osmium oxidation. Accordingly, silyl thioalkene compounds are expected to be useful as a starting material or an intermediate compound in the synthesis of various kinds of organic compounds as a medicine or as an agricultural chemical.

Several methods are proposed in the prior art for the synthetic preparation of certain silyl thioalkene compounds including a method by the photochemical reaction between a silylalkyne compound and a thiol compound under irradiation with light in the presence of a radical initiator and a method by the coupling reaction between a silylalkenyl halide compound and stannyl sulfide in the presence of a catalyst. These methods, however, are industrially not advantageous because the silyl group-containing compound as the starting material cannot be obtained without difficulties. Accordingly, it is eagerly desired to obtain a novel silyl thioalkene compound capable of being synthesized directly from a hydrocarbon compound.

SUMMARY OF THE INVENTION

The present invention accordingly has an object, in view of the above described situations in the prior art, to provide a novel silyl thioalkene compound useful as a synthesis reagent in the field of fine chemicals by an industrially advantageous efficient method by using readily available starting materials.

Thus, the present invention provides, firstly, a silyl thioalkene compound represented by the general formula $$R(-CSAr=CHSiX_3)_n, \quad (I)$$

in which the subscript n is 1 or 2, R is a hydrogen atom or an unsubstituted or substituted monovalent hydrocarbon group, when n is 1, or a divalent hydrocarbon group, when n is 2, Ar is an unsubstituted or nucleus-substituted monovalent aromatic hydrocarbon group and X is a halogen atom or a hydrocarbyloxy group.

The above defined silyl thioalkene compound represented by the general formula (I), in which the group X is a halogen atom, can be prepared by the following methods developed by the inventors.

Firstly, the silyl thioalkene compound of the general formula (I), in which the group X is a halogen atom, denoted by $X^1$ hereinafter, i.e. halogenosilyl thioalkene compound, is prepared by the method, referred to as the first method hereinafter, which comprises the step of:

reacting an alkyne compound represented by the general formula $$R(-C\equiv CH)_n, \quad (II)$$

in which the subscript n is 1 or 2 and R is a hydrogen atom or an unsubstituted or substituted monovalent hydrocarbon group, when n is 1, or a divalent hydrocarbon group, when n is 2, with a silyl sulfide compound represented by the general formula $$ArS-SiX^1_3, \quad (III)$$

in which Ar is an unsubstituted or nucleus-substituted monovalent aromatic hydrocarbon group and $X^1$ is a halogen atom, in the presence of a platinum complex compound as a catalyst.

Alternatively, the silyl thioalkene compound of the general formula (I), in which the group X is a halogen atom, denoted by $X^1$, is prepared by the method, referred to as the second method hereinafter, which comprises the step of:

reacting a disulfide compound represented by the general formula $$ArS-SAr, \quad (IV)$$

in which Ar has the same meaning as defined above, with a hexahalogenodisilane compound represented by the general formula $$X^1_3Si-SiX^1_3, \quad (V)$$

in which $X^1$ has the same meaning as defined above, and an alkyne compound or an alkadiyne compound represented by the general formula $$R(-C\equiv CH)_n, \quad (VI)$$

in which R and n each have the same meaning as defined above, in the presence of a platinum complex compound as a catalyst.

Further, the silyl thioalkene compound of the general formula (I), in which the group X is an unsubstituted or substituted monovalent hydrocarbon group, denoted by $X^2$ hereinafter, can be prepared by the method, referred to as the third method hereinafter, which comprises the step of:

reacting the halogenosilyl thioalkene compound obtained by the first or second method described above and represented by the general formula $$R(-CSAr=CHSiX^1_3)_n, \quad (VII)$$

in which each of the symbols has the same meaning as defined above, with a hydrocarbon carbonium ion-generating compound.

The silyl thioalkene compound of the general formula (I), in which the group X is a hydrocarbyloxy group, denoted by $-OX^2$ hereinafter, is prepared by the method, referred to as the fourth method hereinafter, which comprises the step of:

reacting the halogenosilyl thioalkene compound obtained by the first or second method described above and represented by the general formula (VII) given above with an alcohol compound represented by the general formula $$X^2-OH, \quad (VIII)$$

in which $X^2$ has the same meaning as defined above, in the presence of a dehydrohalogenating agent to effect a dehydrohalogenation reaction.

DETAILED DESCRIPTION OF THE PREFERRED EMBODIMENTS

The silyl thioalkene compound of the present invention represented by the above given general formula (I) is a novel compound not known in the prior art or not described in any literatures although certain related compounds having methyl groups as the groups X in the general formula (I) are disclosed in Journal of the Chinese Chemical Society, volume 43 (1996), page 43, 53–59 and Tetrahedron Letters, volume 30 (1989), pages 2699–2702. When the subscript n in the general formula (I) is 1, the compound is represented by the general formula

R—CSAr=CHSiX$_3$,  (Ia)

in which R is a hydrogen atom or an unsubstituted or substituted monovalent hydrocarbon group and Ar and X each have the same meaning as defined above. When the subscript n in the general formula (I) is 2, the compound is a bis(silyl thioalkene) compound represented by the general formula

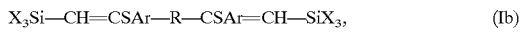

X$_3$Si—CH=CSAr—R—CSAr=CH—SiX$_3$,  (Ib)

in which R is a divalent hydrocarbon group and Ar and X each have the same meaning as defined above.

The monovalent hydrocarbon group denoted by R in the above given general formula (Ia) is exemplified by alkyl groups such as methyl, ethyl, propyl and butyl groups, alkenyl groups such as ethenyl, propenyl and butenyl groups, cycloalkyl groups such as cyclopentyl and cyclohexyl groups, cycloalkenyl groups such as cyclohexenyl group, aryl groups such as phenyl, tolyl, xylyl and naphthyl groups and aralkyl groups such as benzyl and phenethyl groups.

The monovalent hydrocarbon group denoted by R can be substituted by atoms or groups such as halogen atoms and alkoxy, amino, cyano, nitro, alkylcarbonyloxy and acyl groups. Particular examples of such a substituted monovalent hydrocarbon group include 2-chloroethyl, 3-chloropropyl, 4-bromobutyl, 2-methoxyethyl, 3-aminopropyl, 2-cyanoethyl, 3-cyanopropyl, 4-nitrobutyl, tribromodimethyl sulfonylbutyl, tert-butylcarbonyloxyethyl, 4-chlorophenyl and 4-acetylphenyl groups.

The unsubstituted or substituted monovalent aromatic hydrocarbon group denoted by Ar is exemplified by phenyl, 4-chlorophenyl, 4-bromophenyl and 4-methoxyphenyl groups.

The halogen atom denoted by X in the general formula (I) includes atoms of fluorine, chlorine, bromine and iodine. The monovalent hydrocarbon group denoted by X is exemplified by alkyl groups such as methyl, ethyl and propyl groups, cycloalkyl groups such as cyclopentyl and cyclohexyl groups, aryl groups such as phenyl and tolyl groups and aralkyl groups such as benzyl group. The hydrocarbyloxy group denoted by X is exemplified by methoxy, ethoxy, propoxy, cyclohexyloxy, phenoxy and benzyloxy groups.

When the subscript n is 2 to give the general formula (Ib), R is a divalent hydrocarbon group which is exemplified by alkylene groups such as methylene, tetramethylene and pentamethylene groups and arylene groups such as phenylene and naphthylene groups, optionally, substituted by functional groups. Ar and X in the general formula (Ib) can be exemplified by the same atoms and/or groups as those for the general formula (Ia).

The silyl thioalkene compound of the invention represented by the above given general formula (Ia) or (Ib) can be synthetically prepared by either one of the above described first to fourth methods.

In the first method, an alkyne compound or alkadiyne compound represented by the general formula (II) is reacted with the silyl sulfide compound represented by the general formula (III) to give the silyl thioalkene compound of the general formula (I) in which X is a halogen atom.

The alkyne compound represented by the general formula (II) is exemplified by acetylene, butyne, octyne, phenylacetylene, propargyl ether and cyclohexenylacetylene and the alkadiyne compound is exemplified by 1,4-pentadiyne, 1,8-nonadiyne and diethynyl benzene.

The silyl sulfide compound represented by the general formula (III) to be reacted with the alkyne or alkadiyne compound described above is exemplified by trichlorosilyl phenyl sulfide, tribromosilyl phenyl sulfide and trifluorosilyl phenyl sulfide.

In the second method, the above described alkyne or alkadiyne compound of the general formula (II) is reacted with the disulfide compound represented by the general formula (IV) and the hexahalogenodisilane compound represented by the general formula (V) in combination. The disulfide compound of the general formula (IV) is exemplified by diphenyl disulfide, bis(4-chlorophenyl) disulfide, bis(4-bromophenyl) disulfide and bis(4-methoxyphenyl) disulfide. The hexahalogenodisilane compound of the general formula (V) is exemplified by hexachlorodisilane, hexafluorodisilane and hexabromodisilane.

The platinum complex compound used as a catalyst in the reactions of the first and second methods of the invention is preferably a complex compound of platinum in a lower atomic valency or, in particular, a zero-valency platinum complex with tertiary phosphine or phosphite as the ligand, though not particularly limitative thereto. Alternatively, it is optional to use a precursor complex which can readily be converted in situ into a zero-valency platinum complex in the reaction mixture. Further, it is sometimes advantageous to admix the reaction mixture with an appropriate platinum compound without ligands and a tertiary phosphine or phosphite in combination resulting in formation in situ of a zero-valency platinum complex with the tertiary phosphine or tertiary phosphite as the ligand to serve as a catalyst. Various kinds of tertiary phosphines and phosphites can be used as the ligand in the platinum complex to exhibit high catalytic activity although those having excessively high electron donating activity are not always preferable in respect of obtaining a high reaction rate. Examples of preferable ligands include triphenylphosphine, tris(4-chlorophenyl)phosphine, tris(4-fluorophenyl)phosphine, tritolylphosphine, diphenylmethylphosphine, phenyldimethylphosphine, diphenylcyclohexylphosphine, phenyldicyclohexylphosphine, 1,4-bis(diphenylphosphino) butane, trimethyl phosphite and triphenyl phosphite, which can be introduced into the platinum complex either singly or as a combination of two kinds or more.

Some of the examples of other platinum complex compounds without tertiary phosphine or phosphite as the ligand include bis(1,5-cyclooctadiene)platinum and bis (dibenzylideneacetone)platinum. Examples of preferable phosphine- or phosphite-platinum complex compounds include tetrakis (triphenylphosphine)platinum, tris (triphenylphosphine)platinum and ethylenebis (triphenylphosphine)platinum. These platinum complex compounds can be used as the catalyst in the inventive method either singly or as a combination of two kinds or more according to need.

In practicing the first and second methods of the present invention, it is optional that the reaction mixture is diluted by the addition of an organic solvent, which is preferably a hydrocarbon solvent or an ether solvent. The amount of the platinum complex compound added to the reaction mixture as a catalyst is, though not particularly limitative within a range of the so-called catalytic amount, usually 20% by moles or smaller based on the amount of the alkyne or alkadiyne compound as the starting material.

While the reaction mixture in practicing the first and the second methods of the present invention is formed by mixing an alkyne compound or alkadiyne compound with a silyl sulfide compound or a combination of a disulfide compound and a hexahalogenodisilane compound, respectively, it is usually advantageous that the respective reactants are used in a stoichiometric proportion, although a small deviation from the stoichiometric proportion has no particularly adverse influences against proceeding of the reaction. The reaction temperature is usually in the range from room temperature to 300° C. or, preferably, from 50 to 150° C. When the reaction temperature is too low, the reaction does not proceed at a reasonable rate while, when the reaction temperature is too high, the catalytic platinum compound suffers thermal decomposition to decrease the catalytic activity.

The reactions according to the first and second methods of the invention are sensitive to the inhibiting effect of oxygen so that the reaction is performed preferably under an atmosphere of an inert gas such as nitrogen, argon and methane. The desired reaction product, which is a halogenosilyl thioalkene or bis(halogenosilyl thioalkene) expressed by the general formula (Ia) or (Ib), can easily be isolated from the reaction mixture by undertaking a known separating method such as chromatography, distillation and recrystallization.

The third method of the present invention employs the thus obtained halogenosilyl thioalkene or bis(halogenosilyl thioalkene) as one of the starting reagents in the preparation of a silyl thioalkene compound of the general formula (I) in which X is an unsubstituted or substituted monovalent hydrocarbon group. Namely, the above mentioned starting reagent is reacted with a hydrocarbon carbonium ion-generating agent so that the halogen atoms in the starting reagent are replaced with unsubstituted or substituted monovalent hydrocarbon groups. The carbonium ion-generating agent suitable in this case is exemplified by organic lithium compound such as methyl lithium, ethyl lithium, butyl lithium and phenyl lithium and so-called Grignard reagents such as methyl magnesium halides, ethyl magnesium halides, butyl magnesium halides and phenyl magnesium halides. The reaction of the halogenosilyl thioalkene compound with these carbonium ion-generating agent is performed in a reaction mixture of these reagents as diluted, usually, with an ether solvent at a temperature in the range from −20 to +20° C.

The fourth method of the present invention, which is for the preparation of a silyl thioalkene compound of the general formula (I) in which X is a hydrocarbyloxy group, utilizes also the halogenosilyl thioalkene compound obtained by the first or second method as one of the starting reagents. Namely, the halogenosilyl thioalkene compound is reacted with an alcohol compound in the presence of a dehydrohalogenating agent so that the halogen atoms in the starting reagent are replaced with hydrocarbyloxy groups. Examples of the alcohol compounds usable here include methyl alcohol, ethyl alcohol, propyl alcohol, butyl alcohol, phenol and benzyl alcohol. The dehydrohalogenating agent suitable in this case is exemplified by organic basic compounds such as trimethyl amine, triethyl amine and pyridine. The dehydrohalogenation reaction is performed in a reaction mixture diluted with an organic solvent such as hydrocarbon solvents and ether solvents at a temperature in the range from −20 to +20° C.

The desired reaction products produced by the third and fourth methods of the invention can readily be isolated from the respective reaction mixtures by a conventional separating method such as chromatography, distillation and recrystallization.

Thus, the silyl thioalkene compound and the bis(silyl thioalkene) compound represented by the general formulas (Ia) and (Ib), respectively, can be obtained by undertaking the above described first to fourth methods according to the invention.

Identification of the inventive compound can be performed according to a conventional procedure by means of elementary analysis, $^1$H-NMR and $^{13}$C-NMR spectrometric measurements, infrared absorption spectrophotometry, mass spectrometry and others.

In the following, the method of the invention for the preparation of the novel compounds and characterization thereof are described in more detail by way of Examples, which, however, never limit the scope of the invention in any way.

EXAMPLE 1

A reaction mixture was prepared by the addition of, into 1 ml of toluene, 1 mmole of trichlorosilyl phenyl sulfide and 1 mmole of 1-octyne together with ethylenebis(triphenylphosphine)platinum as a catalyst in an amount of 5% by moles based on the amount of sulfur and the reaction mixture was heated at 110° C. for 24 hours under an atmosphere of nitrogen to effect the reaction. The reaction mixture was concentrated by removing toluene followed by distillation under reduced pressure to give a reaction product, which could be identified from the analytical results shown below to be (Z)-2-(phenylthio)-1-(trichlorosilyl)-1-octene which was a novel compound not described in any literatures. The yield of this product was 67% of the theoretical value.

$^1$H-NMR ($C_6D_6$), δ, ppm: 7.21–7.24 (m, 2H); 6.87–6.94 (m, 3H); 5.78 (s, 1H); 1.96 (t, 2H, J=7.4 Hz); 0.95–1.24 (m, 8H); 0.79 (t, 3H, J=7.2 Hz)

$^{13}$C-NMR ($C_6D_6$), δ, ppm: 166.6; 133.0; 129.4; 128.5; 127.2; 123.4; 38.9; 31.6; 28.5; 28.4; 22.7; 14.2

Infrared absorption spectrum (liquid film), $cm^{-1}$: 2960; 2936; 2862; 1562; 1479; 1439; 1069; 1025; 743; 690

Elementary analysis: calculated, %, as $C_{14}H_{19}Cl_3SSi$: C 47.53; H 5.41; found, %: C 47.41; H 5.47

HRMS (EI, 70 eV): calculated: 352.0041; found: 352.0062

EXAMPLE 2

A reaction mixture was prepared by the addition of, into 3 ml of toluene, 1.5 mmoles of hexachlorodisilane, 1.5 mmoles of diphenyl disulfide and 3 mmoles of 1-octyne together with ethylenebis(triphenylphosphine)platinum as a catalyst in an amount of 1.5% by moles based on the amount of sulfur and the reaction mixture was heated at 110° C. for 12 hours under an atmosphere of nitrogen to effect the reaction. The reaction mixture was concentrated by removing toluene followed by distillation under reduced pressure to give a reaction product, which could be identified from the analytical results, which were substantially identical with those in Example 1, to be (Z)-2-(phenylthio)-1-(trichlorosilyl)-1-octene. The yield of this product was 63% of the theoretical value.

EXAMPLE 3

A reaction mixture was prepared by the addition of, into 3 ml of toluene, 1.5 mmoles of hexachlorodisilane, 1.5 mmoles of diphenyl disulfide and 3 mmoles of 1-octyne together with ethylenebis(triphenylphosphine)platinum as a catalyst in an amount of 1.5% by moles based on the amount of sulfur and the reaction mixture was heated at 110° C. for 12 hours under an atmosphere of nitrogen to effect the reaction. The reaction product isolated from the reaction mixture could be identified to be (Z)-2-(phenylthio)-1-(trichlorosilyl)-1-octene from the results of the NMR analysis. The yield of this product was 73% of the theoretical value.

EXAMPLE 4

The reaction mixture after completion of the reaction in Example 3 containing (Z)-2-(phenylthio)-1-(trichlorosilyl)-1-octene was admixed with 30 ml of diethyl ether and the reaction thereof was effected with 9 mmoles of methyl lithium as a 1 mole/liter ether solution at 0° C. for 0.5 hour. With admixture of 10 ml of water, the reaction mixture was extracted with ether and the extract solution was freed from the solvent by distillation under reduced pressure. The residue was subjected to distillation to give a product which could be identified to be (Z)-2-(phenylthio)-1-(trimethylsilyl)-1-octene from the NMR spectrometric analytical data given below. This compound is a novel compound not described in any literatures. The yield of the product was 65% of the theoretical value.

$^1$H-NMR ($C_6D_6$), δ, ppm: 7.32–7.35 (m, 2H); 6.92–7.03 (m, 3H); 6.03 (s, 1H); 2.26 (t, 2H, J=7.1 Hz); 1.11–1.55 (m, 8H); 0.81 (t, 3H, J=6.9 Hz); 0.34 (s, 9H)

$^{13}$C-NMR ($C_6D_6$), δ, ppm: 153.5; 135.9; 135.4; 130.8; 129.2; 126.7; 40.2; 32.0; 28.9; 28.8; 22.9; 14.2; 0.12

$^{29}$Si-NMR ($C_6D_6$), δ, ppm: –9.9

HRMS (EI, 70 eV): calculated as $C_{17}H_{28}SSi$: 292.1661; found: 292.1659

EXAMPLE 5

A reaction mixture was prepared by the addition of, into 3 ml of toluene, 1.5 mmoles of hexachlorodisilane, 1.5 mmoles of bis(4-chlorophenyl) disulfide and 3 mmoles of 1-octyne together with ethylenebis(triphenylphosphine) platinum as a catalyst in an amount of 1.5% by moles based on the amount of sulfur and the reaction mixture was heated at 110° C. for 12 hours under an atmosphere of nitrogen to effect the reaction. The reaction product isolated from the reaction mixture could be identified to be (Z)-2-(4-chlorophenylthio)-1-(trichlorosilyl)-1-octene from the results of the NMR analysis. The yield of this product was 93% of the theoretical value.

EXAMPLE 6

The reaction mixture after completion of the reaction in Example 5 containing (Z)-2-(4-chlorophenylthio)-1-(trichlorosilyl)-1-octene was admixed with 30 ml of diethyl ether and further admixed at 0° C. with 10 mmoles of triethylamine and 10 mmoles of ethyl alcohol to effect the reaction for 0.5 hour. After removal of the precipitates by filtration, the filtrate was concentrated by distillation and the thus concentrated liquid was subjected to liquid chromatography to obtain an isolated reaction product which could be identified to be (Z)-2-(4-chlorophenylthio)-1-(triethoxysilyl)-1-octene from the spectrometric analytical data given below. This compound was a novel compound not described in any literatures. The yield of the product was 83% of the theoretical value.

$^1$H-NMR ($C_6D_6$), δ, ppm: 7.11–7.15 (m, 2H); 6.92–6.97 (m, 2H); 5.94 (s, 1H); 3.97 (q, 6H, J=7.0 Hz); 2.13 (t, 2H, J=7.4 Hz); 1.27–1.43 (m, 2H); 1.25 (t, 9H, J=7.0 Hz); 1.05–1.21 (m, 6H); 0.81 (t, 3H, J=6.8 Hz)

$^{13}$C-NMR ($C_6D_6$), δ, ppm: 157.0; 133.6; 133.4; 133.0; 129.3; 126.3; 58.8; 39.6; 31.8; 28.8; 28.6; 22.8; 18.6; 14.2

$^{29}$Si-NMR ($C_6D_6$), δ, ppm: –61.1

Infrared absorption spectrum (liquid film), cm$^{-1}$: 2976; 2930; 1580; 1477; 1390; 1168; 1083; 961; 820; 774

Elementary analysis: calculated, %, as $C_{20}H_{33}ClO_3SSi$: C 57.60; H 7.97; found, %: C 57.61; H 7.80

HRMS (EI, 70 eV): calculated: 416.1606; found: 416.1496

EXAMPLE 7

Benzylacetylene as a starting reactant was reacted with hexachlorodisilane and bis(4-chlorophenyl) disulfide in the same manner as in Example 5 followed by a further reaction with ethyl alcohol in the same manner as in Example 6 to give (Z)-2-(4-chlorophenylthio)-3-phenyl-1-(triethoxysilyl)-1-propene, which was a novel compound not described in any literatures, in a yield of 76% of the theoretical value.

The results obtained in the analysis of this product were as follows.

$^1$H-NMR (CDCl$_3$), δ, ppm: 7.20–7.33 (m, 7H); 6.99–6.02 (m, 2H); 5.65 (s, 1H); 3.90 (q, 6H, J=7.0 Hz); 3.45 (s, 2H); 1.24 (t, 9H, J=7.0 Hz)

$^{13}$C-NMR (CDCl$_3$), δ, ppm: 156.2; 137.9; 133.7; 133.6; 132.4; 129.1; 129.0; 128.4; 126.6; 125.7; 58.7; 45.6; 18.3

$^{29}$Si-NMR (CDCl$_3$), δ, ppm: –60.8

Infrared absorption spectrum (liquid film), cm$^{-1}$: 2976; 2926; 2888; 1582; 1477; 1390; 1168; 1083; 1013; 961; 822; 754; 698

Elementary analysis: calculated, %, as $C_{21}H_{27}ClO_3SSi$: C 59.62; H 6.43; found, %: C 59.55; H 6.42

HRMS (EI, 70 eV): calculated: 422.1137; found: 422.1154

EXAMPLE 8

(Z)-1-(4-Chlorophenylthio)-1-phenyl-2-(triethoxysilyl) ethene was prepared in the same manner as in Example 7 excepting for replacement of benzylacetylene with phenylacetylene. The yield of this product was 62% of the theoretical value.

The results obtained in the analysis of this product were as follows.

$^1$H-NMR ($C_6D_6$), δ, ppm: 7.46–7.49 (m, 2H); 6.73–7.02 (m, 7H); 6.41 (s, 1H); 3.98 (q, 6H, J=7.0 Hz); 1.26 (t, 9H, J=7.0 Hz)

$^{13}$C-NMR ($C_6D_6$), δ, ppm: 154.2; 140.4; 134.3; 132.5; 131.3; 130.7; 129.3; 128.9; 128.5; 128.1; 59.0; 18.6

Infrared absorption spectrum (liquid film), cm$^{-1}$: 2976; 2888; 1555; 1477; 1446; 1390; 1168; 1081; 963; 777

HRMS (EI, 70 eV): calculated as $C_{20}H_{25}ClO_3SSi$: 408.0981; found: 408.1064

EXAMPLE 9

(Z)-1-(4-Chlorophenyl)-1-(4-chlorophenylthio)-2-(triethoxysilyl)ethene was prepared in the same manner as in Example 7 excepting for replacement of benzylacetylene with 4-chlorophenylacetylene. The yield of this product was 65% of the theoretical value.

The results obtained in the analysis of this product were as follows.

$^1$H-NMR (CDCl$_3$), δ, ppm: 7.45–7.48 (m, 2H); 7.15–7.18 (m, 2H); 7.07–7.08 (m, 4H); 6.17 (s, 1H); 3.92 (q, 6H, J=7.1 Hz); 1.25 (t, 9H, J=7.1 Hz)

$^{13}$C-NMR (CDCl$_3$), δ, ppm: 153.1; 138.5; 134.7; 133.3; 132.5; 131.1; 129.1; 128.9; 128.8; 128.3; 58.9; 18.3

$^{29}$Si-NMR (CDCl$_3$), δ, ppm: −61.9

Infrared absorption spectrum (liquid film), cm$^{-1}$: 2976; 2928; 2890; 1593; 1574; 1555; 1477; 1392; 1168; 1094; 1013; 963; 816; 775

Elementary analysis: calculated, %, as C$_{20}$H$_{24}$Cl$_2$O$_3$SSi: C 54.17; H 5.45; S 7.23; found, %: C 54.47; H 5.39; S 7.51

HRMS (EI, 70 eV): in calculated: 442.0591; found: 442.0492

EXAMPLE 10

(Z)-1-(4-Chlorophenylthio)-1-(4-methylphenyl)-2-(triethoxysilyl)ethene was prepared in the same manner as in Example 7 excepting for replacement of benzylacetylene with 4-methylphenylacetylene. The yield of this product was 60% of the theoretical value.

The results obtained in the analysis of this product were as follows.

$^1$H-NMR (C$_6$D$_6$), δ, ppm: 7.44–7.46 (m, 2H); 6.97–7.01 (m, 2H); 6.75–6.79 (m, 4H); 6.46 (s, 1H); 4.00 (q, 6H, J=7.0 Hz); 1.89 (s, 3H); 1.22 (t, 9H, J=7.0 Hz)

$^{13}$C-NMR (C$_6$D$_6$), δ, ppm: 154.0; 138.9; 137.5; 134.6; 132.4; 131.2; 129.2; 129.1; 128.9; 128.1; 59.0; 20.9; 18.6

$^{29}$Si-NMR (C$_6$D$_6$), δ, ppm: −61.4

Infrared absorption spectrum (liquid film), cm$^{-1}$: 2976; 2926; 2888; 1557; 1506; 1477; 1390; 1168; 1083; 963; 903; 812; 772

Elementary analysis: calculated, %, as C$_{21}$H$_{27}$ClO$_3$SSi: C 59.62; H 6.43; found, %: C 59.85; H 6.32

HRMS (EI, 70 eV): calculated: 422.1136; found: 422.1135

EXAMPLE 11

(Z)-5-Chloro-2-(4-chlorophenylthio)-1-(triethoxysilyl)-1-pentene was prepared in the same manner as in Example 7 excepting for replacement of benzylacetylene with 5-chloro-1-pentyne. The yield of this product was 79% of the theoretical value.

The results obtained in the analysis of this product were as follows.

$^1$H-NMR (CDCl$_3$), δ, ppm: 7.25–7.32 (m, 4H); 5.74 (s, 1H); 3.88 (q, 6H, J=7.1 Hz); 3.42 (t, 2H, J=6.5 Hz); 2.34 (t, 2H, J=7.2 Hz); 1.87–1.93 (m, 2H); 1.23 (t, 9H, J=7.1 Hz)

$^{13}$C-NMR (CDCl$_3$), δ, ppm: 155.5; 133.6; 133.1; 132.3; 129.2; 125.6; 58.7; 43.8; 36.2; 30.9; 18.3

$^{29}$Si-NMR (CDC$^3$), δ, ppm: −61.4

Infrared absorption spectrum (liquid film), cm$^{-1}$: 2976; 2928; 2890; 1580; 1477; 1444; 1390; 1294; 1168; 1083; 1013; 963; 820; 764

Elementary analysis: calculated, %, as C$_{17}$H$_{26}$Cl$_2$O$_3$SSi: C 49.87; H 6.40; found, %: C 49.52; H 6.10

HRMS (EI, 70 eV): calculated: 408.0747; found: 408.0746

EXAMPLE 12

(Z)-5-Cyano-2-(4-chlorophenylthio)-1-(triethoxysilyl)-1-pentene was prepared in the same manner as in Example 7 excepting for replacement of benzylacetylene with 5-cyano-1-pentyne. The yield of this product was 81% of the theoretical value.

The results obtained in the analysis of this product were as follows.

$^1$H-NMR (C$_6$D$_6$), δ, ppm: 6.93–7.03 (m, 4H); 5.76 (s, 1H); 3.92 (q, 6H, J=7.0 Hz); 1.91 (t, 2H, J=7.3 Hz); 1.36 (t, 2H, J=6.8 Hz); 1.15–1.25 (m, 2H); 1.21 (t, 9H, J=7.0 Hz)

$^{13}$C-NMR (C$_6$D$_6$), δ, ppm: 154.2; 133.8; 133.0; 132.7; 129.5; 128.1; 118.8; 58.9; 37.8; 24.0; 18.6; 15.5

$^{29}$Si-NMR (C$_6$D$_6$), δ, ppm: −61.9

Infrared absorption spectrum (liquid film), cm$^{-1}$: 2976; 2928; 2890; 2250; 1580; 1477; 1441; 1390; 1168; 1081; 1013; 963; 820; 777

Elementary analysis: calculated, %, as Cl$_{18}$H$_{26}$ClNO$_3$SSi: C 54.05; H 6.55; N 3.50; found, %: C 53.87; H 6.59; N 3.59

HRMS (EI, 70 eV): calculated: 399.1090; found: 399.1097

EXAMPLE 13

(Z)-6-(tert-Butyldimethylsiloxy)-2-(4-chlorophenylthio)-1-(triethoxysilyl)-1-hexene was prepared in the same manner as in Example 7 excepting for replacement of benzylacetylene with 6-(tert-butyldimethylsiloxy)-1-hexyne. The yield of this product was 72% of the theoretical value.

The results obtained in the analysis of this product were as follows.

$^1$H-NMR (CDCl$_3$), δ, ppm: 7.23–7.32 (m, 4H); 5.68 (s, 1H); 3.86 (q, 6H, J=7.0 Hz); 3.51 (t, 2H, J=6.4 Hz); 2.18 (t, 2H, J=7.4 Hz); 1.21–1.25 (m, 4H); 1.23 (t, 9H, J=7.0 Hz); 0.86 (s, 9H); 0.00 (s, 6H)

$^{13}$C-NMR (CDCl$_3$), δ, ppm: 157.5; 133.4; 133.1; 132.8; 129.1; 123.9; 62.8; 58.6; 38.9; 31.9; 25.9; 24.7; 18.3; 18.2; −5.3

$^{29}$Si-NMR (CDCl$_3$), δ, ppm: 18.5; −60.7

Infrared absorption spectrum (liquid film), cm$^{-1}$: 2932; 2139; 1257; 1168; 1083; 1013; 961; 835; 777

Elementary analysis: calculated, %, as C$_{24}$H$_{43}$ClO$_4$SSi$_2$: C 55.51; H 8.35; S 6.17; found, %: C 55.58; H 8.41; S 6.40

EXAMPLE 14

(Z)-4-(tert-Butylcarbonyloxy)-2-(4-chlorophenylthio)-1-(triethoxysilyl)-1-butene was prepared in the same manner as in Example 7 excepting for replacement of benzylacetylene with 4-(tert-butylcarbonyloxy)-1-butyne. The yield of this product was 87% of the theoretical value.

The results obtained in the analysis of this product were as follows.

$^1$H-NMR (CDCl$_3$), δ, ppm: 7.24–7.32 (m, 4H); 5.78 (s, 1H); 4.12 (t, 2H, J=6.3 Hz); 3.86 (q, 6H, J=7.1 Hz); 2.49 (t, 2H, J=6.3 Hz); 1.21 (t, 9H, J=7.1 Hz); 1.14 (s, 9H)

$^{13}$C-NMR (CDCl$_3$), δ, ppm: 178.3; 152.5; 133.5; 132.8; 132.4; 129.3; 127.8; 61.9; 58.6; 38.7; 38.2; 27.1; 18.2

$^{29}$Si-NMR (CDCl$_3$), δ, ppm: −61.8

Infrared absorption spectrum (liquid film), cm$^{-1}$: 2976; 2930; 1731; 1584; 1477; 1392; 1286; 1156; 1087; 963; 822; 772

Elementary analysis: calculated, %, as C$_{21}$H$_{33}$ClO$_5$SSi: C 54.70; H 7.21; found, %: C 54.54; H 7.27

HRMS (EI, 70 eV): calculated: 460.1504; found : 460.1449

EXAMPLE 15

(Z,Z)-1,3-Bis(triethoxysilyl)-2,7-bis(4-chlorophenylthio)-nona-1,8-diene was prepared in the same manner as in Example 7 excepting for replacement of benzylacetylene with n-nona-1,8-diyne and increase of the amounts of hexachlorodisilane and bis(4-chlorophenyl) disulfide each from 1.5 mmoles to 3.0 mmoles. The yield of this product was 69% of the theoretical value.

The results obtained in the analysis of this product were as follows.

$^1$H-NMR (CDCl$_3$), δ, ppm: 7.23–7.29 (m, 8H); 5.63 (s, 2H); 3.87 (q, 12H, J=6.9 Hz); 2.09 (t, 4H, J=7.5 Hz); 1.34–1.39 (m, 4H); 1.23 (t, 18H, J=6.9 Hz); 1.02–1.05 (m, 2H)

$^{13}$C-NMR (CDCl$_3$), δ, ppm: 157.4; 133.4; 133.0; 132.7; 129.1; 123.9; 58.6; 39.0; 28.1; 27.9; 18.3

$^{29}$Si-NMR (CDCl$_3$), δ, ppm: −60.8

Infrared absorption spectrum (liquid film), cm$^{-1}$: 2976; 2930; 1580; 1477; 1441; 1390; 1294; 1168; 1077; 1013; 961; 820; 777; 745

Elementary analysis: calculated, %, as C$_{33}$H$_{50}$Cl$_2$O$_6$S$_2$Si$_2$: C 54.00; H 6.87; found, %: C 54.32; H 6.70

EXAMPLE 16

(Z)-1-(4-Chlorophenylthio)-1-(1-cyclohexenyl)-2-(triethoxysilyl)ethene was prepared in the same manner as in Example 7 excepting for replacement of benzylacetylene with cyclohexen-1-ylacetylene. The yield of this product was 51% of the theoretical value.

The results obtained in the analysis of this product were as follows.

$^1$H-NMR (C$_6$D$_6$), δ, ppm: 6.92–7.05 (m, 4H); 6.36 (bs, 1H); 6.24 (s, 1H); 3.90 (q, 6H, J=7.0 Hz); 1.98–2.00 (m, 2H); 1.74–1.76 (m, 2H); 1.20 (t, 9H, J=7.0 Hz); 1.11–1.31 (m, 4H)

$^{13}$C-NMR (C$_6$D$_6$), δ, ppm: 154.4; 136.3; 136.2; 132.0; 131.8; 130.1; 128.9; 127.2; 58.9; 27.3; 26.0; 22.9; 21.9; 18.5

$^{29}$Si-NMR (C$_6$D$_6$), δ, ppm: −60.9

Infrared absorption spectrum (liquid film), cm$^{-1}$: 2976; 2928; 1549; 1477; 1390; 1168; 1093; 963; 774; 714

Elementary analysis: calculated, %, as C$_{20}$H$_{29}$ClO$_3$SSi: C 58.16; H 7.08; found, %: C 58.34; H 7.05

HRMS (EI, 70 eV): calculated: 412.1294; found: 412.1395

What is claimed is:

1. A silyl thioalkene compound represented by the general formula $$R(-CSAr=CHSiX_3)_n,$$

in which the subscript n is 1 or 2, R is, when n is 1, a hydrogen atom or an unsubstituted or substituted monovalent hydrocarbon group or, when n is 2, a divalent hydrocarbon group, Ar is an unsubstituted or nucleus-substituted monovalent aromatic hydrocarbon group and X is a halogen atom or a hydrocarbyloxy group.

2. A method for the preparation of a silyl thioalkene compound represented by the general formula $$R(-CSAr=CHSiX^1{}_3)_n,$$

in which the subscript n is 1 or 2, R is, when n is 1, a hydrogen atom or an unsubstituted or substituted monovalent hydrocarbon group or, when n is 2, a divalent hydrocarbon group, Ar is an unsubstituted or nucleus-substituted monovalent aromatic hydrocarbon group and X$^1$ is a halogen atom, which comprises the step of:

reacting an alkyne compound represented by the general formula $$R(-C\equiv CH)_n,$$

in which R and n each have the same meaning as defined above, with a silyl sulfide compound represented by the general formula $$ArS-SiX^1{}_3,$$

in which Ar and X$^1$ each have the same meaning as defined above, in the presence of a platinum complex compound as a catalyst.

3. The method for the preparation of a silyl thioalkene compound as claimed in claim 2 in which the platinum complex compound is a zero-valency platinum complex with tertiary phosphine or phosphite as the ligand.

4. The method for the preparation of a silyl thioalkene compound as claimed in claim 2 in which the reaction of the alkyne compound and the silyl sulfide compound is performed at a temperature in the range from room temperature to 300° C. under an atmosphere of an inert gas.

5. A method for the preparation of a silyl thioalkene compound represented by the general formula $$R(-CSAr=CHSiX^1{}_3)_n,$$

in which the subscript n is 1 or 2, R is, when n is 1, a hydrogen atom or an unsubstituted or substituted monovalent hydrocarbon group or, when n is 2, a divalent hydrocarbon group, Ar is an unsubstituted or nucleus-substituted monovalent aromatic hydrocarbon group and X$^1$ is a halogen atom, which comprises the step of:

reacting a disulfide compound represented by the general formula $$ArS-SAr,$$

in which Ar has the same meaning as defined above, with a hexahalogeno disilane compound represented by the general formula $$X^1{}_3Si-SiX^1{}_3,$$

in which X$^1$ has the same meaning as defined above, and an alkyne compound or an alkadiyne compound represented by the general formula $$R(-C\equiv CH)_n,$$

in which R and n each have the same meaning as defined above, in the presence of a platinum complex compound as a catalyst.

6. The method for the preparation of a silyl thioalkene compound as claimed in claim 5 in which the platinum complex compound is a zero-valency platinum complex with tertiary phosphine or phosphite as the ligand.

7. The method for the preparation of a silyl thioalkene compound as claimed in claim 5 in which the reaction of the disultide compound and the hexahalogenodisilane compound is performed at a temperature in the range from room temperature to 300° C. under an atmosphere of an inert gas.

8. A method for the preparation of a silyl thioalkene compound represented by the general formula $$R(-CSAr=CHSiX^2{}_3)_n,$$

in which the subscript n is 1 or 2, R is, when n is 1, a hydrogen atom or an unsubstituted or substituted monovalent hydrocarbon group or, when n is 2, a divalent hydrocarbon group, Ar is an unsubstituted or nucleus-substituted monovalent aromatic hydrocarbon group and $X^2$ is an unsubstituted or substituted monovalent hydrocarbon group, which comprises the step of:

reacting a halogenosilyl thioalkene compound represented by the general formula $$R(\text{—CSAr}\!=\!\text{CHSiX}^1{}_3)_n,$$

in which the subscript n, R and Ar each have the same meaning as defined above and $X^1$ is a halogen atom, with a hydrocarbon carbonium ion-generating compound.

9. The method for the preparation of a silyl thioalkene compound as claimed in claim 8 in which the hydrocarbon carbonium ion-generating compound is an organolithium compound or a Grignard reagent.

10. The method for the preparation of a silyl thioalkene compound as claimed in claim 8 in which the reaction of the halogenosilyl thioalkene compound and the hydrocarbon carbonium ion-generating compound is performed at a temperature in the range from −20 to +20° C.

11. A method for the preparation of a silyl thioalkene compound represented by the general formula $$R[\text{—CSAr}\!=\!\text{CHSi (OX}^2)_3]\ n,$$

in which the subscript n is 1 or 2, R is, when n is 1, a hydrogen atom or an unsubstituted or substituted monovalent hydrocarbon group or, when n is 2, a divalent hydrocarbon group, Ar is an unsubstituted or nucleus-substituted monovalent aromatic hydrocarbon group and $X^2$ is an unsubstituted or substituted monovalent hydrocarbon group, which comprises the step of:

reacting a halogenosilyl thioalkene compound represented by the general formula $$R(\text{—CSAr}\!=\!\text{CHSiX}^1{}_3)_n,$$

in which the subscript n, R and Ar each have the same meaning as defined above and $X^1$ is a halogen atom, with an alcohol compound represented by the general formula $$X^2\text{—OH},$$

in which $X^2$ has the same meaning as defined above, in the presence of a dehydrohalogenating agent.

12. The method for the preparation of a silyl thioalkene compound as claimed in claim 11 in which the dehydrohalogenating agent is an organic basic compound.

* * * * *